(12) United States Patent
Jensen et al.

(10) Patent No.: US 8,518,123 B2
(45) Date of Patent: Aug. 27, 2013

(54) SYSTEM AND METHOD FOR TISSUE GENERATION AND BONE REGENERATION

(75) Inventors: Peder Jensen, Little Rock, AR (US); Alexandru S. Biris, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 1261 days.

(21) Appl. No.: 11/519,316

(22) Filed: Sep. 11, 2006

(65) Prior Publication Data

US 2007/0061015 A1    Mar. 15, 2007

Related U.S. Application Data

(60) Provisional application No. 60/715,841, filed on Sep. 9, 2005, provisional application No. 60/726,383, filed on Oct. 13, 2005.

(51) Int. Cl.
*A61F 2/28* (2006.01)

(52) U.S. Cl.
USPC .......... 623/23.59; 623/23.51; 623/23.75; 623/23.76

(58) Field of Classification Search
USPC .......... 623/23.51, 23.56–23.58, 23.75–23.76; 427/2.26
See application file for complete search history.

(56) References Cited

U.S. PATENT DOCUMENTS

| | | | |
|---|---|---|---|
| 4,786,501 A | 11/1988 | Janski et al. | |
| 4,814,182 A | 3/1989 | Graham et al. | |
| 4,839,215 A * | 6/1989 | Starling et al. | 428/131 |
| 4,898,734 A | 2/1990 | Mathiowitz et al. | |
| 5,084,051 A * | 1/1992 | Tormala et al. | 606/77 |
| 6,013,591 A | 1/2000 | Ying et al. | |
| 6,025,034 A | 2/2000 | Strutt et al. | |
| 6,096,295 A | 8/2000 | Fuller | |
| 6,110,482 A | 8/2000 | Khouri et al. | |
| 6,129,928 A | 10/2000 | Sarangapani et al. | |
| 6,153,266 A | 11/2000 | Yokogawa et al. | |
| 6,165,486 A | 12/2000 | Marra et al. | |

(Continued)

FOREIGN PATENT DOCUMENTS

| | | |
|---|---|---|
| EP | 0933 089 A2 | 4/1999 |
| EP | 1 270 025 | 5/2006 |

(Continued)

OTHER PUBLICATIONS

David M. Collard, Recent Publications, available at http://www.chemistry.gatech.edu/faculty/Collard.

(Continued)

*Primary Examiner* — Thomas J Sweet
*Assistant Examiner* — Christopher D Prone
(74) *Attorney, Agent, or Firm* — Morris Manning & Martin, LLP; Tim Tingkang Xia, Esq.

(57) ABSTRACT

A system and method for the repair of damaged tissue and bones, congenitally missing tissue/cosmetic reconstruction of tissue is described. The system has a layered porous structure with a sufficiently large area of exposed pores to promote neo-vascularization as well as bone and tissue formation. The disclosed porous implant system can contain bioactive agents necessary for rapid tissue formation and keep ingrowth of unwanted tissue out of the implant surgical site. The implant can be reinforced with an additional, stronger polymer layer and/or may include an endoskeleton or exoskeleton for dimensional stability.

28 Claims, 11 Drawing Sheets

(56) References Cited

U.S. PATENT DOCUMENTS

| | | | |
|---|---|---|---|
| 6,207,218 B1 | 3/2001 | Layrolle et al. | |
| 6,261,322 B1 | 7/2001 | Despres, III et al. | |
| 6,270,347 B1 | 8/2001 | Webster et al. | |
| 6,319,712 B1 | 11/2001 | Meenen et al. | |
| 6,323,146 B1 | 11/2001 | Pugh et al. | |
| 6,398,815 B1 | 6/2002 | Pope et al. | |
| 6,399,215 B1 | 6/2002 | Zhu et al. | |
| 6,399,693 B1 | 6/2002 | Brennan et al. | |
| 6,426,114 B1 | 7/2002 | Troczynski et al. | |
| 6,541,022 B1 | 4/2003 | Murphy et al. | |
| 6,585,992 B2 | 7/2003 | Pugh et al. | |
| 6,610,095 B1 | 8/2003 | Pope et al. | |
| 6,689,375 B1 | 2/2004 | Wahlig et al. | |
| 6,706,273 B1 | 3/2004 | Roessler et al. | |
| 6,730,252 B1 * | 5/2004 | Teoh et al. | 264/178 F |
| 6,840,961 B2 | 1/2005 | Tofighi et al. | |
| 6,852,330 B2 | 2/2005 | Bowman et al. | |
| 6,887,272 B2 | 5/2005 | Shinomiya et al. | |
| 6,899,873 B2 | 5/2005 | Ma et al. | |
| 6,899,876 B2 | 5/2005 | Houston | |
| 2001/0005797 A1 | 6/2001 | Barlow et al. | |
| 2001/0008649 A1 | 7/2001 | Layrolle et al. | |
| 2001/0053406 A1 | 12/2001 | Layrolle et al. | |
| 2002/0016635 A1 | 2/2002 | Despres et al. | |
| 2002/0042657 A1 | 4/2002 | Pugh et al. | |
| 2002/0073894 A1 | 6/2002 | Genge et al. | |
| 2002/0084194 A1 | 7/2002 | Redepenning | |
| 2002/0115742 A1 | 8/2002 | Trieu et al. | |
| 2003/0031698 A1 | 2/2003 | Roeder et al. | |
| 2003/0077311 A1 | 4/2003 | Vyakarnam et al. | |
| 2003/0077398 A1 | 4/2003 | Strutt et al. | |
| 2003/0099630 A1 | 5/2003 | DiBenedetto et al. | |
| 2003/0099762 A1 | 5/2003 | Zhang et al. | |
| 2003/0113686 A1 | 6/2003 | Jia et al. | |
| 2003/0143258 A1 | 7/2003 | Knaack et al. | |
| 2003/0152606 A1 | 8/2003 | Gerber | |
| 2003/0153965 A1 | 8/2003 | Supronowicz et al. | |
| 2003/0165440 A1 | 9/2003 | Roth et al. | |
| 2003/0170378 A1 | 9/2003 | Wen et al. | |
| 2003/0171820 A1 | 9/2003 | Wilshaw et al. | |
| 2003/0180344 A1 | 9/2003 | Wise et al. | |
| 2003/0203038 A1 | 10/2003 | Vail | |
| 2003/0219466 A1 | 11/2003 | Kumta et al. | |
| 2003/0232071 A1 | 12/2003 | Gower et al. | |
| 2004/0024081 A1 | 2/2004 | Trieu et al. | |
| 2004/0082998 A1 | 4/2004 | Shinomiya et al. | |
| 2004/0091547 A1 | 5/2004 | Ben-Nissan et al. | |
| 2004/0126405 A1 | 7/2004 | Sahatjian et al. | |
| 2004/0131562 A1 | 7/2004 | Gower et al. | |
| 2004/0138758 A1 | 7/2004 | Evans et al. | |
| 2004/0153165 A1 | 8/2004 | Li et al. | |
| 2004/0161444 A1 | 8/2004 | Song et al. | |
| 2004/0161996 A1 | 8/2004 | Ward et al. | |
| 2004/0191200 A1 | 9/2004 | Lezer et al. | |
| 2004/0210209 A1 | 10/2004 | Yeung et al. | |
| 2004/0213977 A1 | 10/2004 | Ward et al. | |
| 2004/0236432 A1 | 11/2004 | Hyon et al. | |
| 2004/0247644 A1 | 12/2004 | Bratt et al. | |
| 2004/0249006 A1 | 12/2004 | Gleason et al. | |
| 2004/0249472 A1 | 12/2004 | Liu et al. | |
| 2004/0250729 A1 | 12/2004 | Jang et al. | |
| 2004/0253290 A1 | 12/2004 | Kim et al. | |
| 2004/0254668 A1 | 12/2004 | Jang et al. | |
| 2005/0008672 A1 | 1/2005 | Winterbottom et al. | |
| 2005/0013973 A1 | 1/2005 | Richter et al. | |
| 2005/0019365 A1 | 1/2005 | Frauchiger et al. | |
| 2005/0031704 A1 | 2/2005 | Ahn | |
| 2005/0042252 A1 | 2/2005 | Tanaka et al. | |
| 2005/0053638 A1 | 3/2005 | Tanaka et al. | |
| 2005/0079200 A1 | 4/2005 | Rathenow et al. | |
| 2005/0216081 A1 * | 9/2005 | Taylor | 623/17.11 |
| 2008/0131425 A1 | 6/2008 | Garcia et al. | |

FOREIGN PATENT DOCUMENTS

| | | |
|---|---|---|
| EP | 1 273 312 | 9/2006 |
| JP | 61201019 A | 5/1986 |
| JP | 09308681 A | 2/1997 |
| JP | 11267193 | 5/1999 |
| JP | 2002248119 A | 3/2002 |
| WO | WO-03/088925 A2 | 10/2003 |
| WO | WO-2004/011050 | 2/2004 |
| WO | WO-2004/047880 | 6/2004 |
| WO | WO-2005/086849 | 9/2005 |
| WO | WO-2005/123155 | 12/2005 |

OTHER PUBLICATIONS

Collard Group, Publications, available at http://web.chemistry.gatech.edu/~collard/more/index.html.

"OsteoGraf/LD—Synthetic, Radioipaque, Resorbable Bone," Dentsply Friadent CeraMed, www.ceramed.com/PEPGEN/OSTEOGF_LD_MAIN_PG.shtml, retreived Aug. 5, 2006.

"A Complete Focus on Dental Bone Regeneration and Tissue," Dentsply Friadent CeraMed, www.ceramed.com/PRODUCTS/products_reg.shtml, retreived Aug. 5, 2006.

"OsteoGraf/N—Predictable Increase of Bone Dimension," Dentsply Friadent CeraMed, www.ceramed.com/PEPGEN/OSTEOGF_N_MAIN_PG.shtml, retreived Aug. 5, 2006.

"Clinical, Histologic, and Histomorphometric Evaluation of Mineralized Solvent-Dehydrated Bone Allograft (Puros) in Human Maxillary Sinus Grafts," Noumbissi et al. J. of Oral Implantology. 31:2, 171-79 (2005).

"Human Histologic Analysis of Mineralized Bone Allograft (Puros) Placement Before Implant Surgery," Minichetti et al. J. of Oral Implantology. XXX::2, 74-82 (2004).

"Clinical Case Presenting the Use of Straumann Bone Ceramic for Ridge Preservation in the Mandible," Levin, Barry P., Starget, pp. 17-18 (Jan. 2006).

"Bone Replacement Grafts." J. Periodontal, Academy Report, 76:9, 1603-5 (2005).

"OrthoBlast II: A Powerful Combination for Creating New Bone." Brochure. IsoTis OrthoBiologics. (2004).

INFUSE® Bone Graft. About INFUSE® Bone Graft. Michelson Technology at Work.

"Puros® Pericardium Allograft Membrane." Zimmer Dental. Brochure.

Puros® allografts. Zimmer Dental. Brochure.

* cited by examiner

SYSTEM AND METHOD FOR TISSUE GENERATION AND BONE REGENERATION

CROSS-REFERENCE TO RELATED APPLICATIONS

This application claims the benefit of Provisional Application No. 60/715,841, filed on Sep. 9, 2005, and of Provisional Application No. 60/726,383, filed on Oct. 13, 2005, the contents of which are incorporated herein by reference in their entirety.

BACKGROUND OF THE INVENTION

The invention is directed to a system and method for the repair of damaged tissue and bones, congenitally missing tissue/cosmetic and non-cosmetic reconstruction and/or augmentation of tissue, and more particular to an implant having a porous layered structure with sufficiently large exposed pores to promote neo-vascularization as well as bone and tissue formation. This porous implant system can also contain bioactive agents necessary for rapid tissue formation and keep ingrowth of unwanted tissue out of the implant surgical site.

Bone regeneration and generation of new tissue have become important areas in the treatment of various diseases and in reconstructive surgery. Bone grafts can be used to promote healing of fractures and trauma, to promote osteogenesis, for example, following osteomyelitis, and to augment bone in plastic and reconstructive surgery. Other bone diseases are bone diseases resulting in bone loss are periodontal diseases and osteoporosis. Bone repair materials, therefore, are actively sought for bone repair and regeneration. Biodegradable and biocompatible polymeric compositions are useful for bone grafting, bone repair, bone replacement, or bone-implant fixation purposes.

In periodontal reconstruction or implant fixation, bone graft material must support the structural integrity of the site throughout the course of new bone regeneration. Autografts and allografts are used in current bone graft procedures. Autografts are preferable, but are not always available in sufficient quantities or may not produce a clinically desired result. Bone replacement materials for maxillofacial, alveolar and mandibular reconstruction are in use as alternatives to autografts. Clinically applied techniques include the use of biodegradable membranes for guided tissue regeneration during bone recovery after grafting procedures. However, despite significant advances in the development of these technologies to better approximate the three-dimensional nature of complex tissue equivalents, the development of clinically applicable bone replacement materials has remained a challenge. At least in part, the challenge lies with the difficulty in enabling sufficient ingrowth of repair tissues into biodegradable repair materials for prolonged periods of time to allow the bone architecture to form at the defect site. Implantation of such materials in skeletal repair sites commonly produces new bone growth that is often limited to the periphery of the implant rather than an actual tissue penetration throughout the implant. However, tissue penetration appears eminently important for the successful development and manufacturing of universal tissue equivalents for maxillofacial and periodontal applications.

In past approaches, bio-ceramic fillers have been used to provide the desired mechanical strength and structural integrity of bone reconstruction materials. For example, $Ca_{10}(PO_4)_6(OH)_2$, hydroxyapatite (HA), is a widely-utilized bio-ceramic material for bone repair because it closely resembles native tooth and bone crystal structure. However, sintered HA, while adequate for coatings on porous metal surfaces, tends to be too dense to permit efficient ingrowth of bone.

In one prior art approach, a bioresorbable composition for bone reconstruction was produced from a bioresorbable polymer, a micro- or nano-sized biocompatible filler, and a substance aiding in the creation of pores in the composition. The filler can be HA, the bioresorbable polymer can be a material cross-linkable with a cross-linking monomer, and the pore creating substance can be an effervescent agent such as a carbonate and an acid. However, the pores tend to be isolated, i.e. unconnected, which makes it difficult or impossible for the blood vessels to grow into the composite to a significant depth.

In another prior art approach, a granular material, such as HA, was at least partially embedded in a resorbable polymer film. It was proposed to produce an implant piece in preferably cylindrical form from a cartilage substitute previously. This approach leaves only the ends of the rolled-up sheet exposed for the ingrowth of blood vessels, at least before the polymer film is resorbed in the body.

It would therefore be desirable to provide an implant structure for the regeneration of bone and the generation of tissue with a larger porous surface area and sufficient large pores sizes to permit efficient ingrowth of blood vessels.

It would also be desirable to provide an implant structure with long-term dimensional stability and sized to conform to the size and shape of various implant sites in the body.

It would moreover be desirable to controllably supply and time release as part of the implant structure therapeutic, analgesic and/or antibacterial substances, growth factors, proteins, peptides, drugs, tissue subcomponents including but not limited to bone particles and hydroxy appetite, which promote growth, prevent infections and the like. The bone particles can be autografts, allografts, xenografts (usually bovine) or alloplastic bone grafts (synthetic, such as β-tricalcium phosphate).

It would also be desirable to provide an implant suitable for the generation and/or regeneration of soft tissue, depending on the type of tissue desired.

It would be desirable also to have an implant suitable to permit in growth of blood vessels yet keep unwanted tissue from growing into the surgically placed implant during healing.

SUMMARY OF THE INVENTION

The systems and methods described herein relate to an implant structure which facilitates formation of bone and soft tissue.

According to one aspect of the invention, a biocompatible implement for bone and tissue regeneration has a layered structure with alternating layers formed of a bioresorbable polymer carrier and of a bone or tissue forming material applied to a major surface of the polymer carrier. The side faces of the bone or tissue forming material are at least partially uncovered to allow neo-vascularization when the implement is in contact with an implant surgical site.

According to another aspect of the invention, a method for producing a biocompatible implement for bone and tissue regeneration includes the steps of applying a bioresorbable polymer layer on a substrate, depositing a layer of a bone or tissue forming material on the polymer layer, and continue to alternatively applying a polymer layer and a bone/tissue forming layer to produce a layered structure having alternating layers formed of the bioresorbable polymer and the bone or tissue forming material.

According to yet another aspect of the invention, a method for producing a biocompatible implement for bone and tissue regeneration includes applying a bioresorbable polymer layer on a substrate, depositing a layer of a bone or tissue forming material on the polymer layer, and removing from the substrate the composite layer formed of the bioresorbable polymer layer and the layer of the bone or tissue forming material. A layered structure of alternating polymer and bone/tissue layers can thereby be produced by stacking several composite layers formed with the aforedescribed process.

Embodiments of the invention may include one or more of the following features.

The bioresorbable polymer carrier may be a resorbable or degradable synthetic polymer. To increase the surface area of the implant in contact with the surgical site, a major surface of the layer formed of the bone or tissue forming material facing away from the polymer carrier may also be uncovered.

The alternating layers may be arranged in the form of a stack and/or or rolled up and may be shaped to conform to the shape of the implant site. The various layers of the stack may be "tied" together by one or more connecting strips extending along side faces of the stack. The multilayer implant structure can be made more rigid by incorporating in the polymer layer a reinforcing or support layer and/or by incorporating an exo- or endoskeleton. Either one can be made of a biocompatible polymer material or of a biocompatible metal.

The layered structure may be covered with an additional layer made of a biocompatible polymer selected to prevent ingrowth of unwanted cells from the implant site. In one embodiment, a layer made of a bioactive material may be placed between the polymer carrier and the layer formed of the bone or tissue forming material. In one embodiment, the bone or tissue forming material may be applied to both major surfaces of the polymer carrier.

The bioresorbable polymer layer may applied from a solution containing the polymer, or alternatively from polymer particles. Likewise, the layer of the bone or tissue forming material may be deposited from a solution containing the bone or tissue forming material, or from bone or tissue particles. When deposited from solution, the solvent of the solution containing the bone or tissue forming material is preferably identical to or at least compatible with the solvent of a solution containing the bioresorbable polymer.

Further features and advantages of the invention will be apparent from the following description of illustrative embodiments.

BRIEF DESCRIPTION OF THE DRAWINGS

These and other features and advantages of the invention will be more fully understood by the following illustrative description with reference to the appended drawings, in which like elements are labeled with like reference designations and which may not be to scale.

DETAILED DESCRIPTION OF CERTAIN ILLUSTRATED EMBODIMENTS

Figure 1A:
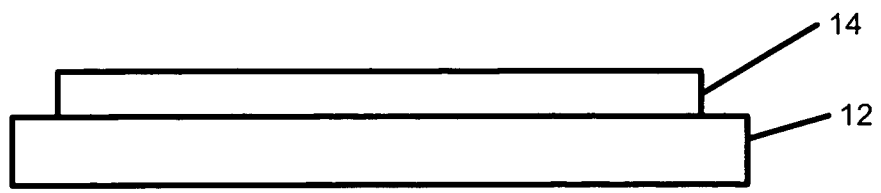
FIGS. 1A to 1E depict schematically a process for growth of a bone or tissue implant structure according to an embodiment of the invention.

The invention, in various embodiments, provides systems and methods for repairing bone and tissue and/or for promoting formation of new bone and tissue, and more particularly for an implant structure with sufficient porosity to allow efficient ingrowth of blood vessels (neo-vascularization), while minimizing the risk of infection and/or rejection. The system is capable of providing support for growth and/or deposition of one or more platelets, stem cells, bone marrow cells, blood cells, and/or newly formed or immature cells in order to initiate the bone/tissue growth and is capable of at least partially including (although is not limited to) the following elements: at least one polymer matrix (which is preferably biodegradable, at least partially biocompatible, possesses a hydrophilic surface, has strong mechanical rigidity, and allows cellular growth); one or more bone particles; one or more proteins, enzymes, and/or drugs to promote bone and/or tissue generation and/or regeneration; one or more peptides; one or more stem cells and/or progenitor cells; one or more blood cells and/or platelets; one or more HA structures and/or nanostructures disclosed elsewhere herein; and/or one or more collagens or carbohydrates. The proteins, enzymes, and/or drugs may optionally be mixed in the polymer matrix and/or placed on the surface of the system. Included on the inside or on the surface of the polymeric matrixes may be one or more nanograf particles, nanoparticles, structures, and/or nanostructures of HA and/or collagen particles, nanoparticles, structures, or nanostructures.

The proposed system is highly porous, biocompatible, and allows for vascular ingrowth for bone/tissue regeneration. The surface should not inhibit any biological entity from interacting and to be hydrophilic or potentially become hydrophilic under different conditions or processes. Suitable materials for building structures for tissue/bone engineering and (re-) generation are certain polymers, ceramics, carbon-based materials and metals and metal composites. The bone regeneration system may include nano structures or microstructures, which may include bismouth nano structures, and HA. The nano structures or microstructures may instead include, for example, biocompatible polymer fibers and/or particles having diameters of approximately 5 nm to approximately 3000 nm and lengths of a few nanometers to one or more millimeters, preferably polyglycolic acid (PGA); metal nano structures or microstructures such as titanium dioxide ($TiO_2$) or other forms of titanium; cromaflex; and/or carbon nanostructures or microstructures such as multi-wall tubes, multi-wall carbon nanotubes or microtubes, nanofibers or microfibers, or human demineralized bone. When PGA is utilized, the HA is incorporated into the PGA nanofibers and at the surface of the bone defect. The PGA also advantageously dissolves into carbon dioxide ($CO_2$) and water and is capable of intermixing with other substances in it. Alternately, both PGA and titanium (e.g., $TiO_2$) nanostructures or microstructures may be mixed together and coated with HA to formulate the bone regeneration material. The titanium substance may be added to the mixture to desirably alter the density of the nano structure or microstructure portion of the bone regeneration material.

The proposed system has a layered structure composed of a polymeric material that may contain other substances, such as bioactive substances or substances promoting the generation of tissue growth, both within the layers and on the surface of the layers. Some of the bioresorbable polymers may or may not require enzymes in order to degrade. The layered, porous design with unobstructed sidewalls (columns) gives this system a very high surface area for neo-vascularization and the growth of cells necessary for tissue regeneration. In addition, stem cells, osteoblasts, and other types of suitable cells can be incorporated into the system to aid in tissue generation.

The implant system can assume different shapes and dimensions as may be required for a particular application. The system is capable of being formed in various shapes and sizes based on the shape and size of the bone or tissue mass which is required to be generated and/or regenerated. For example, the system may exist in one or more of the following shapes: strips, fibers, membranes, corrugations, spheres, spirals, cones, sandwiched layers, cylinders, or any other known shape or combination thereof. The implant can be properly positioned in the surgical site with medical pins, screws, or other devices.

Polymers can degrade by several mechanisms. The most common mechanism is diffusion. Two types of diffusion-controlled systems have been developed; the first is a reservoir device in which the bioactive agent (drug) forms a core surrounded by an inert diffusion barrier. These systems include membranes, capsules, microcapsules, liposomes, and hollow fibers. The second type is a monolithic device in which the active agent is dispersed or dissolved in an inert polymer. As in reservoir systems, drug diffusion through the polymer matrix is the rate-limiting step, and release rates are determined by the choice of polymer and its consequent effect on the diffusion and partition coefficient of the drug to be released Bioresorbable devices are eventually absorbed by the body, for example, by conversion of a material that is insoluble in water into one that is water/liquid-soluble, and thus need not be removed surgically.

As for other biomaterials, the basic design criteria for polymers used in the body call for compounds that are biocompatible, processable, sterilizable, and capable of controlled stability or degradation in response to biological conditions. The reasons for designing an implant that degrades over time often go beyond the obvious desire to eliminate the need for retrieval. For example, the very strength of a rigid metallic implant used in bone fixation can lead to problems with "stress shielding," whereas a bioresorbable implant can increase ultimate bone strength by slowly transferring load to the bone as it heals. For drug delivery, the specific properties of various degradable systems can be precisely tailored to achieve optimal release kinetics of the drug or active agent.

An ideal biodegradable polymer for medical applications would have adequate mechanical properties to match the application (strong enough but not too strong), would not induce inflammation or other toxic response, would be fully metabolized once it degrades, and would be sterilizable and easily processed into a final end product with an acceptable shelf life. In general, polymer degradation is accelerated by greater hydrophilicity in the backbone or end groups, greater reactivity among hydrolytic groups in the backbone, less crystallinity, greater porosity, and smaller finished device size.

A wide range of synthetic biodegradable polymers have been developed, including polylactide (PLA), polyglycolide (PGA), poly(lactide-co-glycolide) (PLGA), poly(e-caprolactone), polydioxanone, polyanhydride, trimethylene carbonate, poly($\beta$-hydroxybutyrate), poly(g-ethyl glutamate), poly(DTH iminocarbonate), poly(bisphenol A iminocarbonate), poly(ortho ester), polycyanoacrylate, and polyphosphazene. There are also a number of biodegradable polymers derived from natural sources such as modified polysaccharides (cellulose, chitin, dextran) or modified proteins (fibrin, casein).

To date, the compounds that have been employed most widely are PGA and PLA, followed by PLGA, poly(e-caprolactone), polydioxanone, trimethylene carbonate, and polyanhydride. Some of the common PLA products include tissue screws, tacks, and suture anchors, as well as systems for meniscus and cartilage repair.

Other materials could be tyrosine-derived polycarbonate poly(DTE-co-DT carbonate), in which the pendant group via the tyrosine—an amino acid—is either an ethyl ester (DTE) or free carboxylate (DT). Through alteration of the ratio of DTE to DT, the material's hydrophobic/hydrophilic balance and rate of in vivo degradation can be manipulated. It was shown that, as DT content increases, pore size decreases, the polymers become more hydrophilic and anionic, and cells attach more readily.

These materials are subject to both hydrolysis (via ester bonds) and oxidation (via ether bonds). Degradation rate is influenced by PEO molecular weight and content, and the copolymer with the highest water uptake degrades most rapidly.

These polymeric materials can also be developed in such a way that they are stable in the biological environment, and degrade only under specific enzymatic conditions (plasmin, etc.). These materials can also include partially expressed fragments of human or animal fibrin such that the system degrades only in contact with plasmin.

An exemplary process for the growth of the proposed implant structure is illustrated in FIG. 1A to FIG. 1E. As shown in FIG. 1A, the implant structure can be fabricated as one or more layers 14 (only one layer is shown) of a biocompatible polymer on a smooth surface 12, such as Teflon-PTFE. The polymer is preferably in solution mixed with a suitable solvent, and other substances can be added to the solution, for example, collagen, drugs, proteins, peptides, hydroxyapetite crystals (HA), antibiotics, depending on the type of tissue to be grown. The solution can be sonicated to promote mixing of the constituents.

The polymer layers can be applied from solution by one of the following processes: electrospraying, ionization spraying, vibratory dispersion (including sonication), nozzle spraying, compressed-air-assisted spraying and/or by brushing or pouring the solution.

The polymers can be applied and/or allowed to dry or harden under ambient or reduced pressure, exposed to ambient air or to a gas, for example, an inert gas. Processing under reduced pressure can increase the porosity of the layers. The polymer layers can be plasma-treated/activated/electrosprayed to functionalize the surface of the polymer sheets. Surface treatment of polymer layers can improve the hydrophilicity of the layers and promote the colonization with cells and the adhesion of bone particles, such as HA. The surface can also be functionalized by electron or ion bombardment, laser irradiation and/or by any other physical or chemical surface reaction that affects the bonds near the surface. These processes can also help in sterilization of the implant.

Figure 1B:
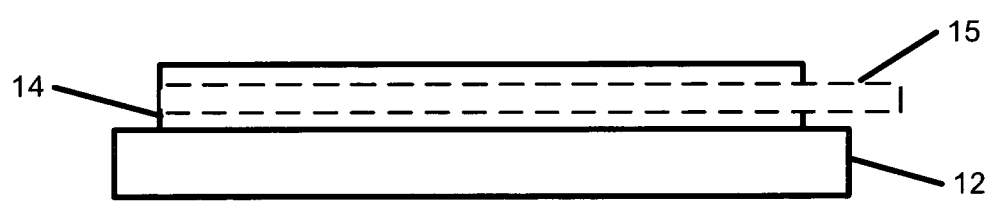

As shown schematically in FIG. 1B, the surface area exposed to the ambient can be increased by placing removable elongated members 15, such as threads, wires, rods on a substrate 12 and depositing the biocompatible polymer layer 14 around the members 15, which may be coated with a biocompatible lubricant, such as Teflon®. After the polymer or the finished implant structure (to be described below) has cured, the members 15 may be removed, for example, pulled out, creating a very porous structure. Although the rods are shown in the depicted exemplary embodiment as being oriented in the plane of the polymer layer 14, they may be oriented in any suitable direction with respect to the polymer layer. The elongated members 15 can have a diameter between approximately 0.01 mm and 10 mm, depending on the size of the implant structure and the dimensions of the various layers.

Figure 1C:
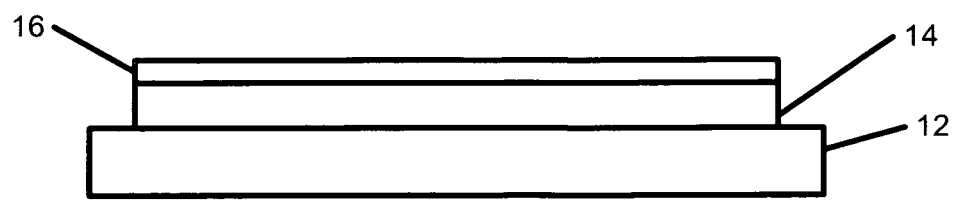

Turning now to FIG. 1C, bioactive materials, such as proteins/peptides, HA, drugs, growth factors, antibiotics (such as tetracycline), and bone morphogenic protein, can be sprayed on the surface of the polymer layer 14, as indicated by layer 16, and/or incorporated in the polymer structures to promote bone growth. The polymer matrix/surface may optionally include proteins and/or enzymes or peptides for rapid bone and/or tissue generation and/or regeneration.

Figure 1D:
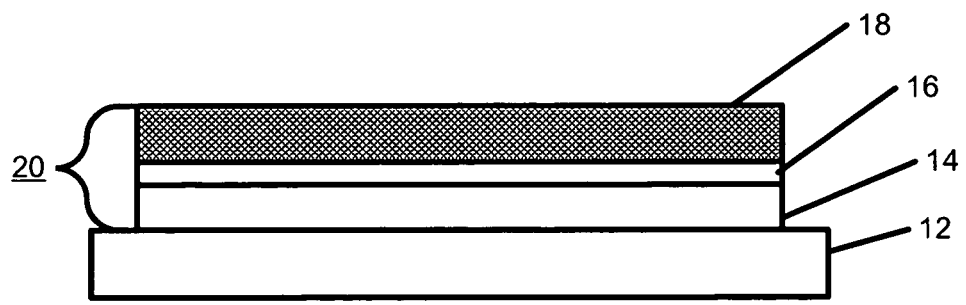

After a sheet (layer) of the polymer 14, which may include the bioactive substances mentioned above or optionally a separate layer 16 with the bioactive substances and/or nanoparticle or microparticle HA, is deposited in the manner described above, a layer 18 consisting of bone particles is deposited thereon, as depicted in FIG. 1D. The bone particles may also be applied from solution incorporating the same solvent as the solvent of the polymer layers, thereby promoting adhesion between the polymer layer 14/separate layer 16 and the bone particles. The bone particles, as well as solid polymer particles, can also be deposited by tribo-charging (friction charging), corona charging, radioactive charging, induction charging, and/or electrochemical charging, while the underlying polymer layer is curing to promote adhesion of the bone particles to the polymer. The nano-/micro-bone particles can have an average particle size from between several nanometers to about 10 μm for the nanoparticles and between about 10 μm and 5 mm for the microparticles. Because the bone particles can be viewed as closely packed spheres, continuous channels having an equivalent pore size in the order of, for example, about 10 to 300 μm, depending on the size of the bone particles, are formed between the bone particles, which is adequate for ingrowth of blood vessels.

The thickness of the layer 18 made of the bone particles can range from several micrometers to several millimeters depending on the implant site. The thickness of the biocompatible polymer layers 14, 16 can also range from several micrometers to several millimeters. It should be noted that the aforedescribed elongated members 15 (see FIG. 1B) may also be placed in the layer 18 (not shown) to increase the accessible surface area of layer 18.

The layered structures can be built up by electrostatic deposition where layers with opposite electronic/electric charges are electrostatically held together. For example, the surface of the polymer layer 14, 16 may be negatively charged by exposure to a plasma, electrostatic corona discharge, ions or electron bombardment and bone particles may be applied to the top surface, optionally also the bottom surface, with the substrate 12 removed, of the polymer layer 14, 16 with an electrosprayer having a friction charger to positively charge the bone particles. The bone layer can hold a surprisingly large charge of approximately 0.1-10 μC/g. This electrostatic process is also useful in improving the adhesion of proteins and amino acids to the surface of the implant.

Figure 1E:
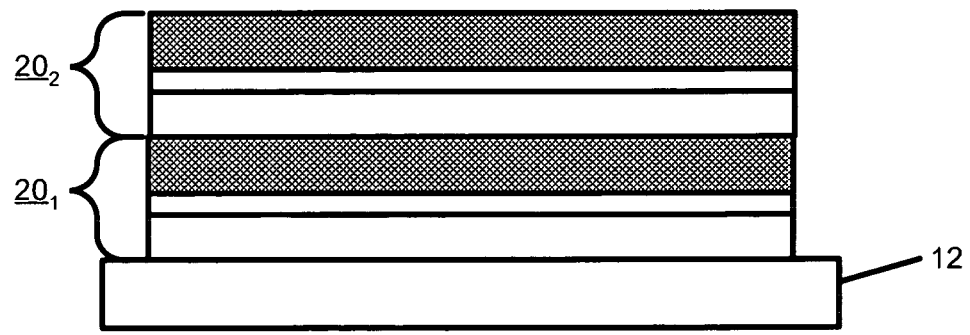
Figure 2:
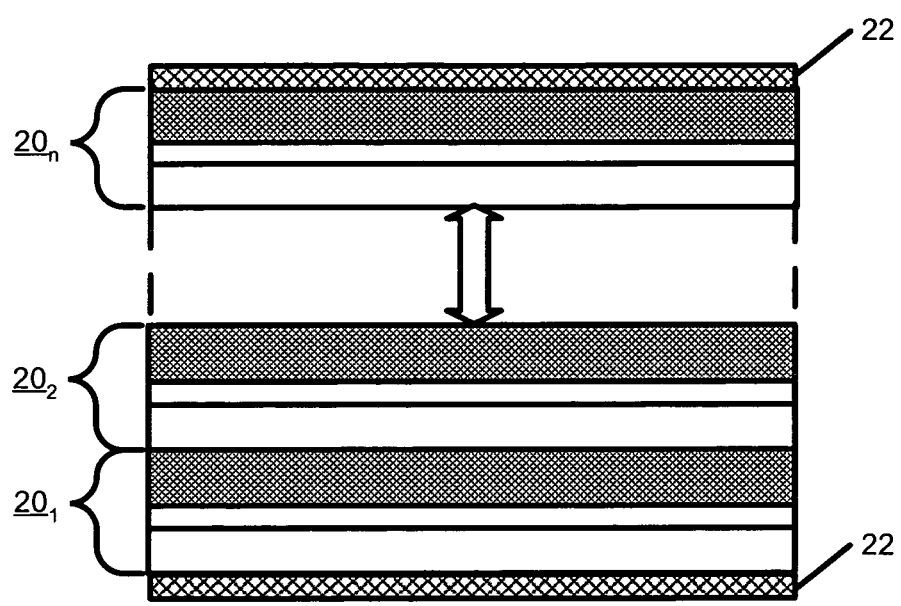
FIG. 2 depicts schematically a layered bone or tissue implant structure fabricated with the process of FIG. 1.

The implant structure of the invention is formed by forming a stack 20 of layers 14, 16 of biocompatible polymer and bone particles 18 (FIG. 1D), and stacking successive stacks $20_1, 20_2, \ldots, 20n$ on top of one another, as indicated in FIG. 1E and FIG. 2. As also shown in FIG. 2, a layer 22 of bone morphogenic protein can be applied (e.g., sprayed) over the bone particles and/or polymer layer to promote bone growth. As mentioned above, the polymer carrier layers 14 and the bone particle layers 18 can have a thickness between approximately 0.1 mm and approximately 5 mm, but are typically less than 3 mm. The layers can be mechanically stacked or applied in situ on top of one another.

Figure 10:
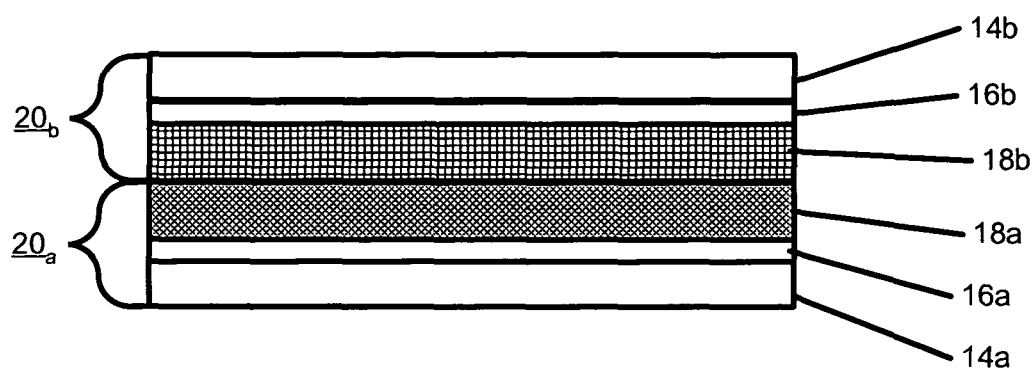
FIG. 10 depicts schematically another embodiment of a layered bone or tissue implant structure fabricated with the process of FIG. 1.

To further increase the porosity, one of the layers may be inverted based on the specific needs of the surgeon and tissue to be generated. In the exemplary embodiment shown in FIG. 10, two (or more) bone particle layers 18a, 18b may be laid on top of each other and supported by respective top 14b and bottom 14a polymeric layers at. On the bottom layer 20a, only the underside of the bone particle layer 18a contacting the polymer layer 14a, shown here with an interposed bioactive layer 16a, would adhere to the bottom layer 14a and 16a, respectively. Conversely, on the top layer $20_b$, only the topside of the bone particle layer 18b contacting the top polymer/bioactive layer 14b, 16b would adhere to the top polymer/bioactive layer. When these two layers $20_a, 20_b$ are placed one on top of each other, with the bone particles of the respective layers facing each other, a considerably thicker bone particle layer is formed from the combination of layers 18a and 18b, which greatly increases the porosity of the implant system. As a direct result of this, although the porosity is increased, the mechanical shear strength is reduced, which may be compensated by applying a more rigid polymer on the lateral sides of the implant structure, as described below with reference to FIGS. 4A and 4B.

Figure 11:
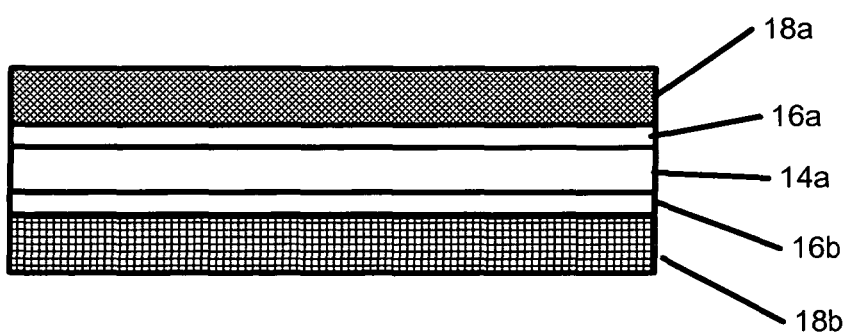
FIG. 11 depicts schematically another embodiment of a layered bone or tissue implant structure.

In another embodiment depicted in FIG. 11, bone particle layers 18a, 18b may be applied to both sides of the polymer layer 14a, with optional interposed bioactive layers 16a, 16b, respectively. The stack 20n may have a square, rectangular, circular shape or any other shape that conforms or can be made to conform to the surgical implant site.

Figure 3:
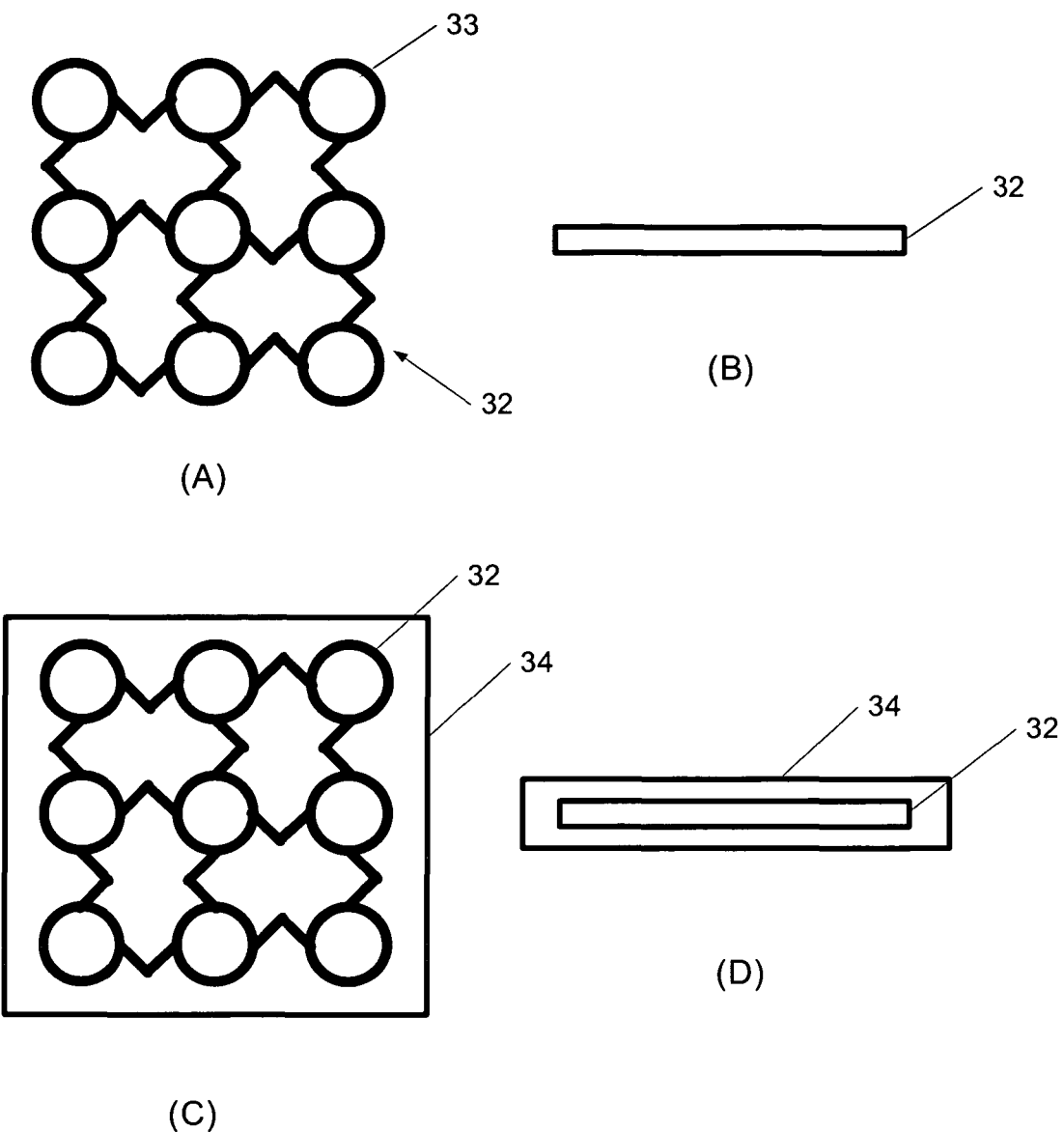
FIGS. 3A to 3D depict schematically a process for growth of a polymer layer of the implant structure of FIG. 1 with a reinforcing sheet for added rigidity.

The biocompatible polymer material is selected so as to be resorbed in the body preferably no faster than the ingrowth of the blood vessels in order to maintain the structural integrity of the implant. However, as illustrated in FIG. 3, the mechanical properties of the bioresorbable polymer layer 14 may be altered by incorporating into one, into several or into all polymer layers of the implant structure a sheet 33 made of a more rigid bioresorbable polymer or of a biocompatible metal, such as titanium, which may have an open structure which allows adjustment of the sheet's rigidity. FIG. 3A shows a top view of such sheet 32, and FIG. 3B shows a cross-sectional view. The sheet may have openings 33 configured to receive a fastener, such as a surgical screw, by which the implant structure having the sheet 32 can be attached to tissue or bone. As indicated in FIG. 3D, the reinforcing sheet 32 may be placed on the substrate 12 (not shown in FIG. 3D) and encapsulated by a second bioresorbable polymer layer 34. Particularly desirable is to form a scaffold having a biostable polymer portion of the scaffold sandwiched inside two biodegradable polymer portions. The combination of the layers 32 and 34 can then take the place of any of the polymer layers in the implant structure depicted in FIG. 2. The second polymer layer may be made of a more rapidly dissolving polymer that will release bioactive substances, such as proteins, drugs, collagen, bone morphogenic proteins, peptides, antibiotics previously mentioned, for bone/tissue regeneration.

Figure 4A:
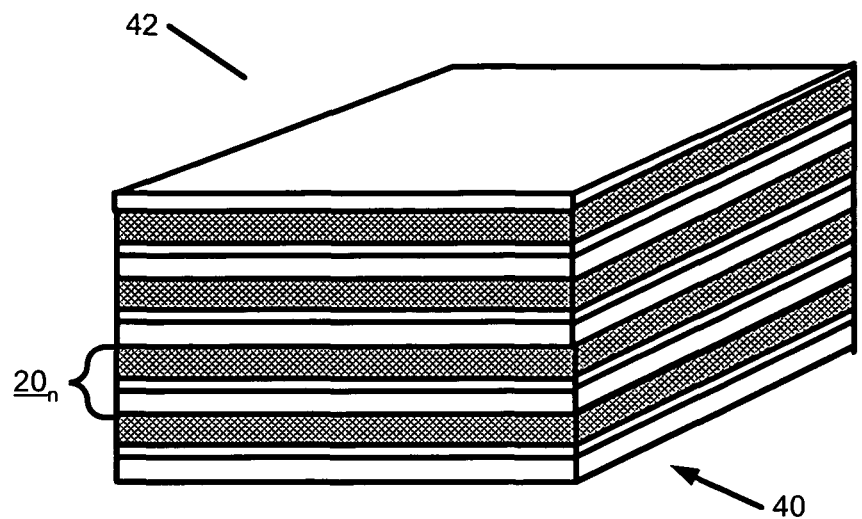
FIGS. 4A and 4B depict schematically a layered bone or tissue implant structure with lateral reinforcing straps.
Figure 4B:
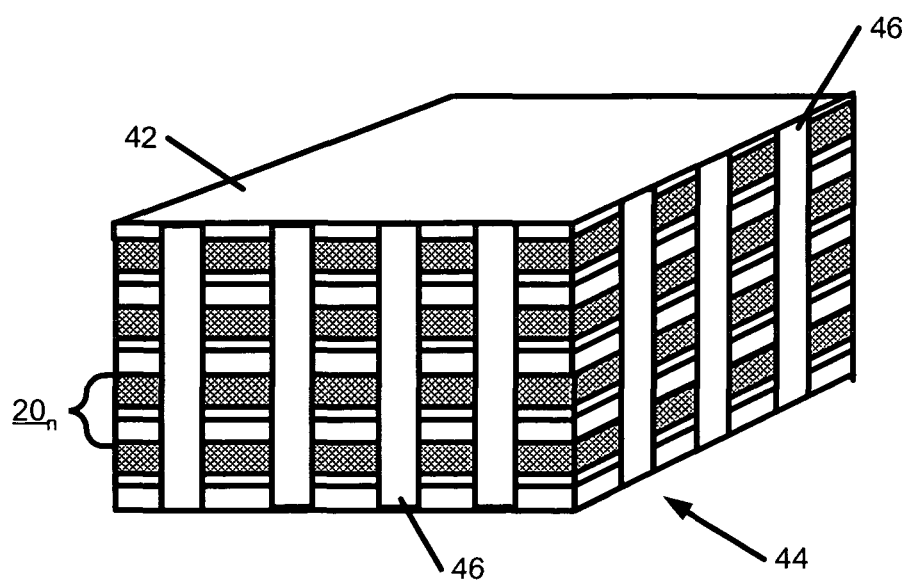

FIGS. 4A and 4B show the implant structure of FIG. 2 in a perspective view 40, clearly illustrating the four-sided open structure which enables rapid neo-vascularization. The top layer 42 can be identical to layer 22 and include bone morphogenic protein and other bioactive materials; alternatively, the top layer of the stack may be made of a material that forms a barrier for penetration of epithelial and endothelial cells, but allows fluids to pass through.

Because the various stacked layers $20_1$, $20_2$, ..., $20_n$ incorporate the same or a similar solvent, the layers adhere together and do not require additional support along the sides for stability. However, to provide added rigidity, a fine layer 46 of a polymer can be applied in a columnar pattern on the outside surfaces of the implant stack in a direction perpendicular to the layers $20_n$, as shown in FIG. 4B. The columns can be spaced from between about 0.5 mm to about 5 mm. The columnar polymer structure can also be surface treated (e.g., in a plasma) to enhance tissue growth, and may can also include nanoparticles HA, bioactive materials, bone morphogenic proteins, and/or stem cells and/or osteoblasts. The incorporation of stem cells will be described later in conjunction with application of the aforedescribed structures for tissue generation.

Implants may be shaped to fit the implant site, for example, be in the form of a cube having a height of several millimeters to about one centimeter and a width and length of between about 0.5 cm and 3 cm, but could be smaller or larger depending on the size of the defect or the augmentation site. As seen for example in FIG. 4A, the layers on the sides of the cube are exposed, thereby promoting ingrowth of blood vessels and the formation of bone or tissue.

In another exemplary embodiment, periodontal barriers may be incorporated for the controlled delivery of chemotherapeutic agents such as tissue regenerative agents like growth factors, antibiotics, and anti-inflammatory agents to promote periodontal healing and regeneration. Therapeutic agents may be incorporated for timed release of these agents in situ. For example, agents may be incorporated into the polymeric matrix and are slowly released as the matrix is degraded. Growth factors, particularly platelet-derived growth factors (PDGF) and insulin-like growth factor (IGF-1), are known to stimulate mitogenic, chemotactic and proliferate (differentiate) cellular responses. The growth factor can be, but is not limited to, one or more of the following: platelet derived growth factors (PDGF), e.g., PDGF AA, PDGF BB; insulin-like growth factors (IGF), e.g., IGF-I, IGF-II; fibroblast growth factors (FGF), e.g., acidic FGF, basic FGF, β-endothelial cell growth factor, FGF 4, FGF 5, FGF 6, FGF 7, FGF 8, and FGF 9; transforming growth factors (TGF), e.g., TGF-P1, TGF β1.2, TGF-β2, TGF-β3, TGF-β5; bone morphogenic proteins (BMP), e.g., BMP 1, BMP 2, BMP 3, BMP 4; vascular endothelial growth factors (VEGF), e.g., VEGF, placenta growth factor; epidermal growth factors (EGF), e.g., EGF, amphiregulin, betacellulin, heparin binding EGF; interleukins, e.g., IL-1, IL-2, IL-3, IL-4, IL-5, IL-6, IL-7, IL-8, IL-9, IL-10, IL-11, IL-12, IL-13, IL-14; colony stimulating factors (CSF), e.g., CSF-G, CSF-GM, CSF-M; nerve growth factor (NGF); stem cell factor; hepatocyte growth factor, and ciliary neurotrophic factor.

Preferred pharmaceutically active materials are those that enhance tissue regeneration and/or tissue adhesion. Illustrative examples include growth factors, antibiotics, immunostimulators, and immuno-suppressants. In one embodiment, the pharmaceutically active material may be a bone morphogenic protein such as BMP. In another embodiment, the pharmaceutically active material may be a growth factor such as FGF or an agent which promotes the generation of connective tissue.

Once the layered implant structure 40 is complete, it can be vacuum-dried to remove residual solvent. The implant structure is relatively rigid with some resiliency.

Figure 5:
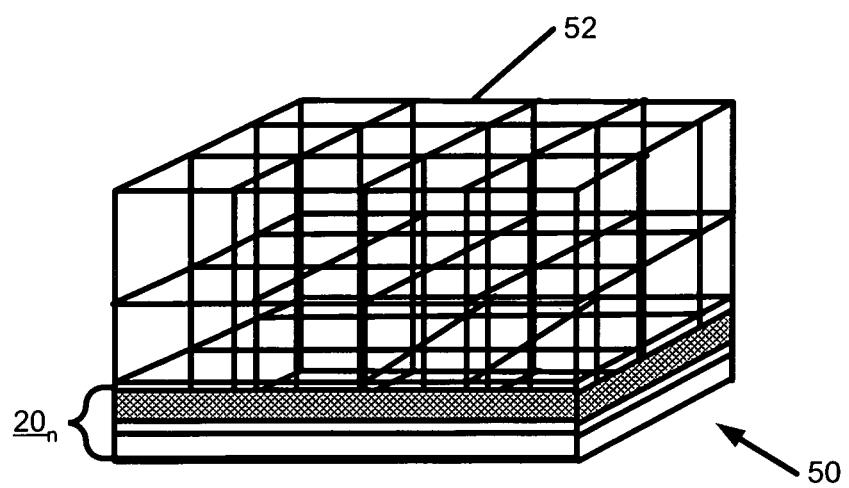
FIG. 5 depicts schematically an endoskeleton with an exemplary implant layer incorporated in the skeleton.
Figure 6:
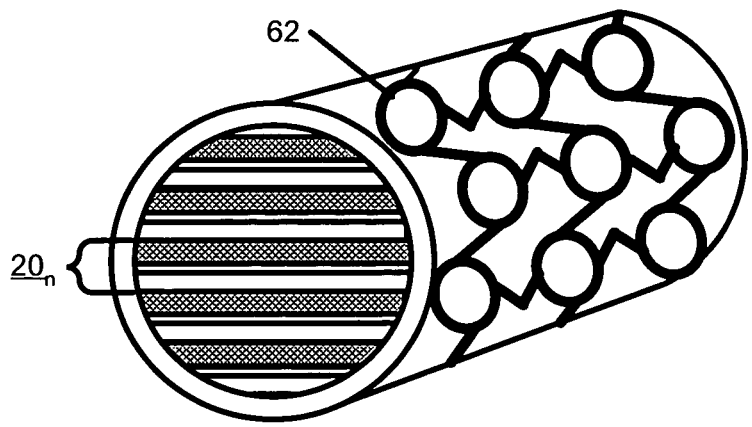
FIG. 6 depicts schematically a first embodiment of an exoskeleton surrounding a layered bone or tissue implant structure of the invention.
Figure 7:
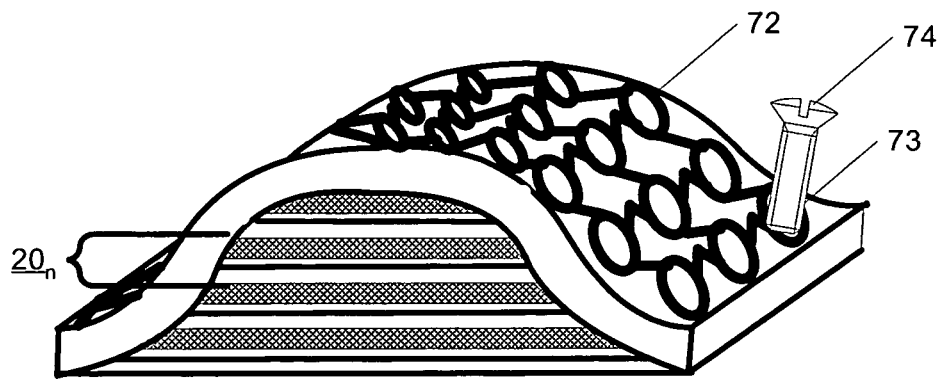
FIG. 7 depicts schematically a second embodiment of an exoskeleton configured for attaching a layered bone or tissue implant structure to surrounding tissue/bone.

As shown in FIGS. 5 to 7, the implant structure can be configured to retain its dimensional stability after implantation and/or be provided with mechanical attachment members, such as lugs or O-rings, for attachment to tissue or bone formation at the implant site by forming structure 50 made of the layers $20_n$ (only one layer is shown so as not to obscure the drawing) inside a skeleton 52 (endoskeleton) made of a biocompatible metal, such as a titanium wires 52, and/or a rigid polymer, or by surrounding the layers $20_n$ with a skeleton (exoskeleton) 62 (FIG. 6) and 72 (FIG. 7). This titanium/rigid polymer endoskeleton or exoskeleton can be formed either as an unwoven mesh or can be woven from fine titanium wires or polymer fibers. In one embodiment, the titanium/polymer mesh may have a thickness from about 1 μm to about 1 mm, whereas the titanium wire/polymer fiber may have a diameter between about 1 μm and 1.5 mm. The wire and mesh 72 can have openings 73 or loops for attachment to the bone via screws/clamps or other mechanical fasteners 74. Since the skeleton 52, 62, 72 is essentially open, the various layers $20_n$ can be deposited by the same process (e.g., electro-spraying) discussed before.

The polymer/titanium mesh or wire can be in many shapes or forms to support the high surface area, porous, polymer based layers, either externally or internally. Exemplary shapes are, for example, a basket-like, cylindrical, sinusoidal, helical, etc.

In one embodiment, the HA can be bonded to the metal (Ti) surface, for example, by plasma-spraying, in order to enhance biocompatibility and mechanical support.

The compositions can be used as scaffolds or fixtures for regeneration of bones or tissues of any type. In one embodiment, the compositions can be used as scaffolds in periodontal tissue regeneration such as regeneration of soft tissue to cover exposed tooth roots surfaces and gingival augmentation, cementum, or bone regeneration. In another embodiment, the compositions/systems can be used as fixtures for bone regeneration, such as regeneration of spinal segments/spinal fusion, periodontal defects, mandible and/or maxillary ridge augmentation, cleft palate, maxillary sinus augmentation or repair of bony cranial defects. In still another embodiment, the composition can be used as bone repair material such as for a bone fracture or osteomyolitis (i.e., not to replace bone but to facilitate healing). In the case of osteomyolitis antibiotics can be incorporated within the polymer structure and released over desired time periods. In one preferred embodiment, the compositions can be used as a bone graft extender to enhance new bone formation in conjunction with allo-, auto-, alloplast, and/or xenograft materials.

The bone repair or tissue regeneration can be any type of bone repair, specifically oral reconstruction, spinal segment repair, bone graft extension. In one specific embodiment, the bone repair is either periodontal, alveolar, or maxillary regeneration. In one particular embodiment, the bone repair is tooth replacement. In another embodiment, the bone repair may include cranial/cranial facial reconstruction, wherein an appropriate template is fabricated ex vivo in a desired shape and then implanted in an appropriate implant site, where the template governs the shape of the new bone and tissue material to be formed. The system/template can be fabricated by using the data from a CT scan or/and an MRI.

In addition to bone repair, the process of the invention can be used to construct layered structures that may include cells for the generation of tissue. The term cell as used herein means any preparation of living tissue, inclusive of primary tissue explants and preparations thereof, isolated cells, cell lines (including transformed cells) and host cells. Preferably, autologous cells are employed. However, xenogenic, allogenic, syngeneic cells, or stem cells may also be useful.

Tissue can be grown in vitro and then implanted (for example, for growth of connective tissue/coronary vessels for arterial grafts). Alternatively, tissue can also be grown in vivo by implanting a layered structure made of a bioresorbable polymer and stem cells or other types of suitable cells (liver cells for the growth of liver tissue; myocardial cells, muscle cells for replacing/restoring damaged heart tissue; epithelial cells, connective tissue cells for skin grafts; osteblasts for bone generation).

Suitable living cells for use with the tissue implant include, but are not limited to, epithelial cells (e.g., keratinocytes, adipocytes, hepatocytes), neurons, glial cells, astrocytes, podocytes, mammary epithelial cells, islet cells, endothelial cells (e.g., aortic, capillary and vein endothelial cells), and mesenchymal cells (e.g., dermal fibroblasts, mesothelial cells, osteoblasts), smooth muscle cells, striated muscle cells, ligament fibroblasts, tendon fibroblasts, chondrocytes, fibroblasts, and any of a variety of stem cells. Also suitable for use in the tissue implant are genetically modified cells, immunologically masked cells, and the like. Appropriate extracellular matrix proteins (ECM) may be added to the tissue implant structure to further promote cell ingrowth, tissue development, and cell differentiation within the scaffold. ECM proteins can include one or more of fibronectin, laminin, vitronectin, tenascin, entactin, thrombospondin, elastin, gelatin, collagen, fibrillin, merosin, anchorin, chondronectin, link protein, bone sialoprotein, osteocalcin, osteopontin, epinectin, hyaluronectin, undulin, epiligrin, and kalinin.

Additional biologically active macromolecules helpful for cell growth, morphogenesis, differentiation, and tissue building, include growth factors, proteoglycans, glycosaminoglycans and polysaccharides. These compounds are believed to contain biological, physiological, and structural information for development or regeneration of tissue structure and function.

Figure 8A:
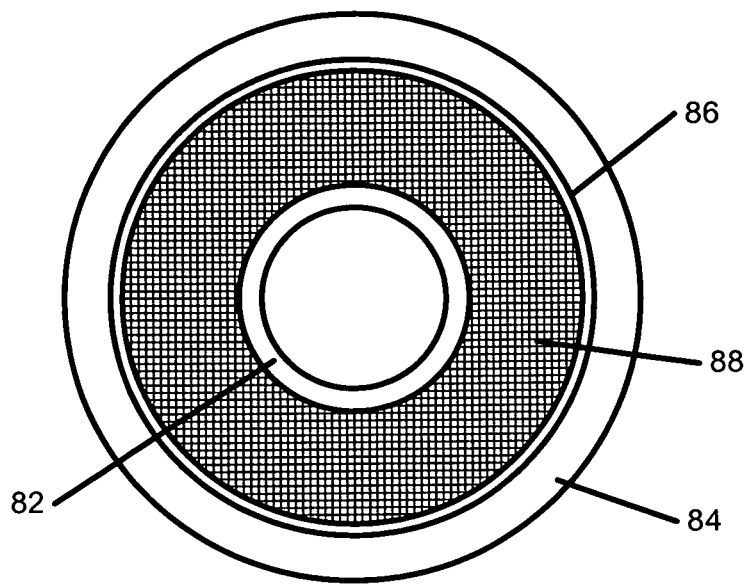
FIGS. 8A and 8B depict schematically an exemplary embodiment of tissue generation with the process of the invention.
Figure 8B:
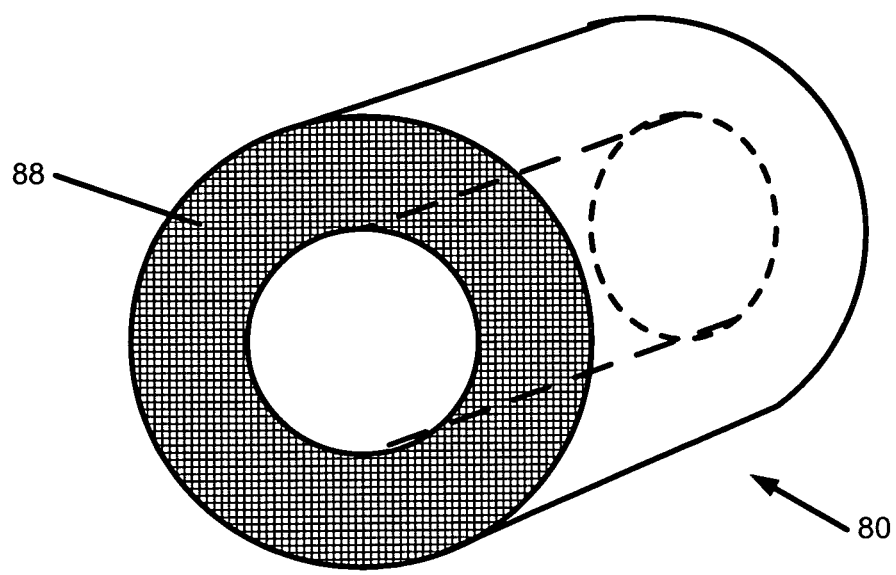

As depicted schematically in FIG. 8A in a cross-sectional view, a coronary vessel may be formed by shaping around an optional cylindrical support 82, which can be made of a biodegradable material, a layer of stem cells or connective tissue cells 88, which may have been deposited on a bioresorbable polymer layer 84, optionally coated with a layer 86 of bioactive materials, such as, but not limited to, proteins, drugs, hormones, tissue growth factors, FGF, platelet derived growth factors and the like. The structure of FIG. 8A can be cultured in vitro and harvested, forming a vessel 80 made of connective tissue 88 that can be grafted to an organ, such as the heart.

Returning now to FIGS. 1 and 2, for growing tissue in vitro or in vivo, the bone particles contained in layer 18 may be replaced with or added to stem cells or other types of suitable cells, such as epithelial cells, connective tissue cells and the like, as described above. Layer 16 could then contain, instead or in addition to nanoparticle HA, also proteins, drugs, hormones, tissue growth factors, platelet derived growth factors and the like. For repair of damaged skin tissue, the layer 16 may also contain antibiotics to thwart infection. For in vivo growth of damaged tissue, layer 14 may be made of a relatively soft bioresorbable polymers so as to better conform to the shape and possible movement of the affected organ. Other biologically active agents such as nutrients, cytokines, angiogenic factors, and immunomodulatory factors are also expected to aid the cells in thriving in the bone/tissue layer.

Figure 9A:
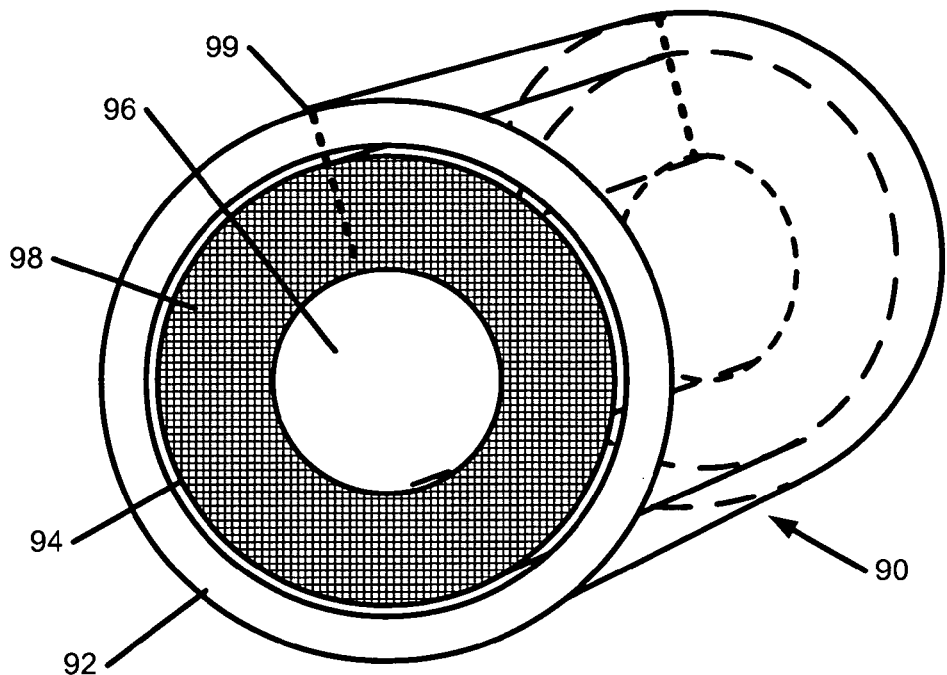
FIGS. 9A and 9B depict schematically a bone or tissue implant structure rolled in a hollow cylinder and stacked.
Figure 9B:
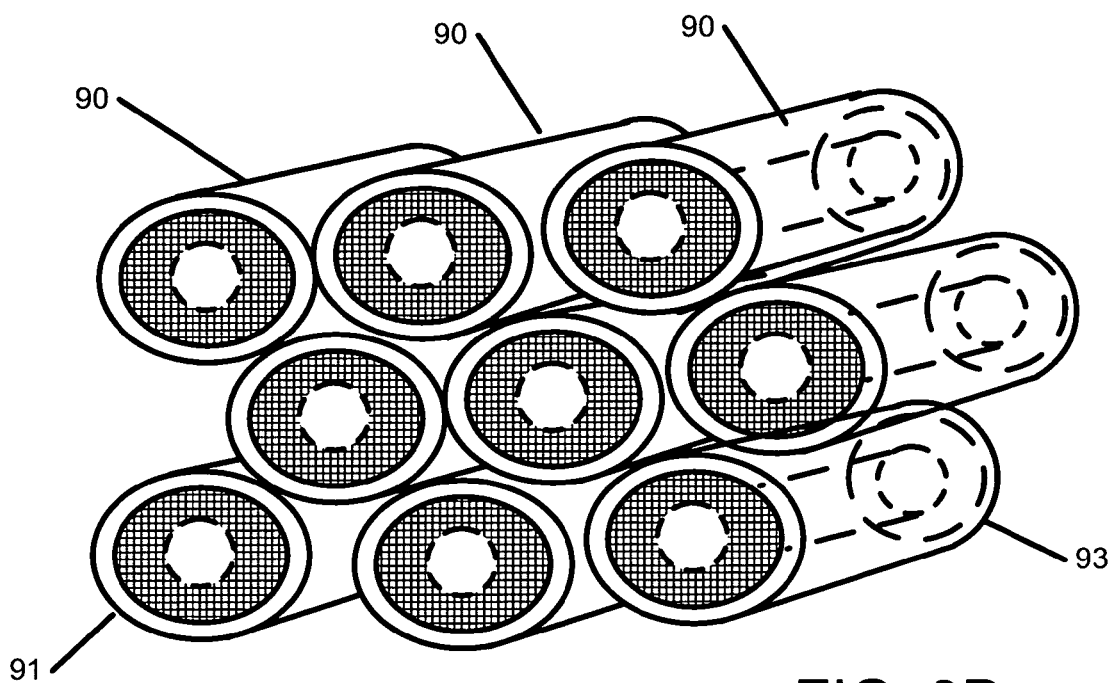

In another exemplary embodiment of a porous implant structure depicted in FIGS. 9A and 9B, sheets of the type illustrated in FIG. 2, coated with either a layer of bone particles 98 or a layer of connective tissue 98 and the like for tissue growth on or in a layer of bioresorbable polymer 92, which is optionally coated with bioactive materials 94, may be rolled into a hollow cylinder 90, with both ends open and the lengthwise edges of the sheets joined along seam 99. The cylinders 90 may then be stacked on top of one another lengthwise (see FIG. 9B), leaving large open porous sections with exposed bone particles/ tissue cells at the respective ends 91, 93 and inside the hollow space 96. Due to the large surface area, this structure is also expected to promote neo-vascularization while, unlike injected unrestrained bone particles, preventing the bone particles/ tissue cells from exiting the implant site. The polymeric matrixes may exist in a number of shapes including but not limited to one or more membranes, porous membranes, corrugated surfaces of different shapes, spirals, cones, particles, rolled sheets, stacked sheets, films of different thicknesses, spheres, cylinders, any other known shape, or a combination of any of the preceding shapes. Optionally, a number of porous polymeric sheets coated with one or more HA particles/nanoparticles, bone particles/nanoparticles, collagen, enzymes, proteins, and/or peptides for bone and/or tissue growth may be stacked upon one another such that the resulting system possesses a large surface area and a variable thickness.

Figure 12:
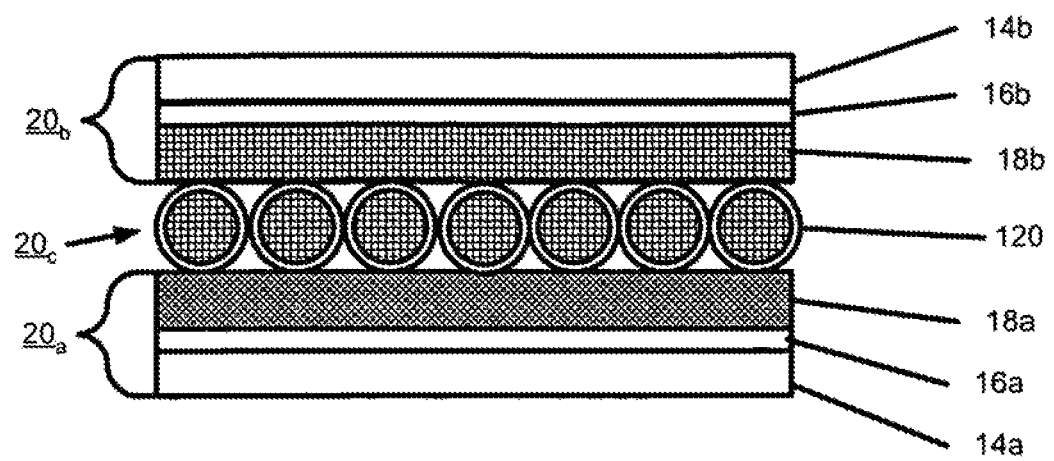
FIG. 12 depicts schematically yet another embodiment of a layered bone or tissue implant structure employing the cylindrical structure of FIG. 9A.

In yet another embodiment of an implant structure according to the invention depicted in FIG. 12, hollow cylinders 120 of, for example, a type described above with reference to FIG. 9A may be inserted in form of layer $20_c$ between the layers $20_a$ and $20_b$. This arrangement produces an open structure with enhanced surface area for neo-vascularization.

Figure 13:
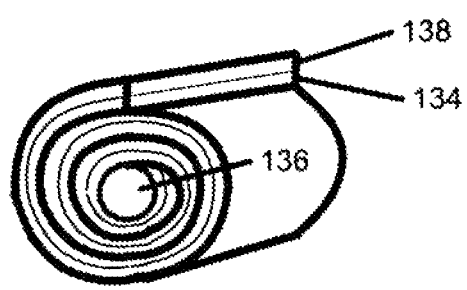
FIG. 13 depicts schematically an embodiment of a rolled-up bone or tissue implant structure.

In another embodiment of an implant structure of the invention depicted in FIG. 13, the different aforedescribed embodiments of layered implant sheets 134, 138 can also be rolled up, forming a helical structure when viewed in cross-section. To further increase the surface area of the exposed bone/tissue layer, the interior can include a hollow space 136, similar to the hollow space 96 in FIG. 9B.

In yet another exemplary embodiment (not shown), bone particles may be encapsulated in a bioresorbable polymer layer which may optionally be coated with bioactive materials of a type described above, which can then be deposited (e.g., sprayed) to create a highly porous structure. In a separate embodiment of the present invention (not shown), the system may further include one or more stem cells to promote any kind of tissue or bone generation and/or regeneration. In this embodiment, the polymeric matrix provides structure for the stem cells, and when implanted in the human body or tissue culture, enables the growth of new tissue and/or bone. For example, a system can be composed of hollow polymeric structures (not shown) which are preferably biocompatible and at least partially biodegradable but support in and/or on their surfaces one or more stem cells, blood cells, platelets, and/or bone marrow cells that initiate tissue and/or bone growth.

Clinical Studies

The disclosed layered implant structure was placed inside of tooth extraction sockets in 28 human patients with informed consent. The implant systems were composed of a layered system of polymer and xenograft/bovine bone particles with 0.25 to 1 mm diameter in size. Nano-sized and/or micro-sized HA were introduced in the polymer layers. The implant shape ranged in size from 4 to 5 mm in diameter and up to 10 mm in length and was roughly cylindrically shaped. The polymer consisted of hydrophilic, biocompatible, biodegradable polyurethane based polymer.

The microparticle or nanoparticle layered implant structures described herein can be used to support the reconstructive process by allowing (1) high density of ingrowing bone cells within the scaffold, (2) integration of the ingrowing tissue with surrounding tissue following implantation, (3) vascularization, and (4) cosmetic recovery.

The polymers used in the clinical studies are hydrophilic thermoplastic polyurethanes sold, for example, under the name HydroThane™ by Cardiotech International, Inc., Wilmington, Mass. (USA). Bone particles are available, for example, from Osteohealth Company, Division of Luitpold Pharmaceuticals, Inc., Shirley, N.Y. (USA), under the name Bio-Oss®. Bio-Oss® is a natural, osteoconductive bone substitute that promotes bone growth in periodontal and maxillofacial osseous defects. Nanoparticle/microparticle HA is commercially available, for example, from Berkeley Advanced Biomaterials, Inc.

In a typical surgical implant procedure, the diseased tooth was extracted and the layered polymer/bone particle structure of the invention was placed in the extraction site. The site was then sutured, and the healing process was documented 2-weeks post-op, 8 weeks post-op and 4-months post-op. After 4 months of healing, i.e., 4-months post-op, the surgical site was opened, showing hard, dense, and normal appearing bone. For each patient, a bone core was removed via trephine to asses the mechanical and microscopic properties. Then a Ti root form implant was placed. Notably, the implant could be safely placed only 4-months post-op, whereas the Bio-Oss® package insert explicitly states that implantation of titanium fixtures should not take place until about 6 months after the use of Bio-Oss® in any implant site, thus demonstrating clearly the advantages of the implant structure of the invention over conventional materials.

Excellent healing was observed in all 28 cases, with no failures or rejections. The results compare favorably with control experiments performed (1) without placement of any foreign material in the extraction site; and (2) placing bone particles only in the extraction site. In the first case, approximately only 60% of the extraction site was filled with immature bone after 4-months post extraction. In the second case, where bone particles were implanted, healing was normal in all controls with regard to clinical appearance. However, it is important to note that upon surgical re-entry 4-months after placement of the bone particles in the extraction site, the bone was soft and rubbery and crumbled when disturbed. This bone, when removed from the trephine, was so soft and crumbly, and could be pulled apart with two fingers.

Conversely, when bone structure from the layered implant according to the invention was removed with a trephine 4-months after implant, the bone was dense and hard, and had the appearance of normal bone. It was resistant to heavy mechanical pressure in the range of 50-100 psi, and a minimum of 90% bone fill was observed in all extraction sites.

It appears that the faster bone formation and healing process with the layered bone implant according to the invention can be attributed to the larger exposed porous surface area which promotes neo-vascularization through the connected channels formed throughout the implant structure. The implant site does not need to be covered with epithelium, as the material will stay in place and not wash out. The epithelium will rapidly grow over the top layer of polymer. The top layer of layered implant structure of the invention can also be made of a slower dissolving polymer, thereby obviating the need to surgically close the implant site. Conversely, the implant site implanted with bone particles only, which disadvantageously produced only soft bone due to the inability of blood vessels to penetrate into the densely packed bone particles, always needed to be covered with epithelium to prevent the bone particles from washing out.

The favorable outcome of the clinical trials demonstrates that the layered polymer/bone particle structure of the invention, with HA nanoparticles and microparticles embedded in the bio-resorbable polymer layer, produces bone growth with the following characteristics not offered by materials currently used in surgery for tissue augmentation:

Superior handling ability, it would stay in the defect and not wash out during surgery;

Implanted material does not require covering;

Denser bone was formed at 4-months, which may be attributable to higher porosity and larger exposed surface area, and contact between nanoparticle HA with the incoming blood cells that enhance bone formation at the contact site;

The degradation rate of the polymer can be matched to the rate of bone/tissue growth, which allows the nanoparticle HA to remain at the surgical site for faster bone growth. For example, the bioresorbable polymer carrier layer may include a polymer having a resorption rate in the implant site that substantially matches a rate of neo-vascularization in the layer formed of the bone or tissue forming material;

Polymers offer the potential for surface modification and incorporation of bio-active substances mentioned earlier, which can also accelerate bone formation.

While the invention has been disclosed in connection with the preferred embodiments shown and described in detail, various modifications and improvements thereon will become readily apparent to those skilled in the art. For example, the implant structure may have any shape and form adapted be received by the implant site. The implant may be grown in vitro or in vivo. Structures may be reinforced with a dimensionally stable polymer or metal framework which can be shaped and sized prior to deposition of the bone particles. The composites can be manufactured through a compounding and compression molding process or by electrostatic deposition or by spraying of layers. The hardness of the implant can be varied as a function of the specific requirement by introducing more or less minerals in its composition, through selection of suitable polymers, and/or by using a more rigid polymer/metal endoskeleton or exoskeleton. The size of the pores (open or closed) can be controlled in such a way that the dissolution rate is in a range required for a particular application. Layered planar, rolled and coiled (helical) implant structures may be combined in any manner suited for the intended implant site and procedure, and may be configured for growth of bone and/or tissue. Accordingly, the spirit and scope of the present invention is to be limited only by the following claims.

What is claimed is:

1. A biocompatible implement for bone and tissue regeneration, comprising:
a first layered structure and a second layered structure, each having:

a bioresorbable polymer carrier layer having opposing, plasma treated, major surfaces, made of a polymer having a resorption rate in an implant site that substantially matches a rate of tissue generation in the layers formed of the bone or tissue forming material; and a bone or tissue forming material layer including nanosized hydroxyapetite particles and being applied to at least one of the major surfaces of the polymer carrier layer, wherein the bone or tissue forming material layer has at least one side face, and wherein the at least one side face of the bone or tissue forming material layer is at least partially uncovered to allow neovascularization when the implement is in contact with an implant surgical site; and a geometric structure layer having a plurality of substantially cylindrical geometric structures and positioned between the bone or tissue forming material layers of the first and second layered structures, wherein the substantially cylindrical geometric structures are aligned parallel to the first and second layered structure, wherein the substantially cylindrical geometric structures each have a bioresorbable polymer layer and a cylindrical bone or tissue forming material, the bioresorbable polymer layer being adjacent to the bone or tissue forming material layers of the first and second layered structures and surrounding the cylindrical bone or tissue forming material.

2. The implement of claim 1, wherein the bioresorbable polymer carrier layers comprise at least one resorbable or degradable, synthetic polymer.

3. The implement of claim 1, further comprising a second layer of bone or tissue forming material, wherein in addition to the side faces, a major surface of the second layer formed of the bone or tissue forming material faces away from an adjacent polymer carrier layer is also uncovered.

4. The implement of claim 1, wherein the layers are arranged in a planar structure forming a stack.

5. The implement of claim 1, further comprising a layer made of a bioactive material interposed between one of the polymer carrier layers and the layer formed of the bone or tissue forming material.

6. The implement of claim 1, wherein the layer of bone or tissue forming material comprises a bone forming material comprises at least one material selected from the group consisting of tricalcium phosphates, mixed calcium phosphates calcium carbonate, bone particles of zenograft, allografts, autografts, and/or alloplastic grafts.

7. The implement of claim 1, wherein at least one of the bioresorbable polymer carrier layers comprises a support layer coextensive with the at least one polymer carrier layer over at least a portion of a major surface of the at least one polymer carrier layer.

8. The implement of claim 7, wherein the support layer is formed as a mesh with openings throughout the support layer.

9. The implement of claim 1, wherein the bioresorbable polymer carrier layer has a thickness of between approximately 0.1 mm and approximately 5 mm.

10. The implement of claim 1, wherein the bioresorbable polymer carrier layer has a thickness of between approximately 0.1 mm and approximately 3 mm.

11. The implement of claim 1, wherein the layer formed of the bone or tissue forming material has a thickness of between approximately 0.1 mm and approximately 5 mm.

12. The implement of claim 1, wherein the layer formed of the bone or tissue forming material has a thickness of between approximately 0.5 mm to approximately 3 mm.

13. The implement of claim 1, wherein at least one of the bioresorbable polymer carrier layers further comprises at least one nanosized or microsized material within the at least one bioresorbable polymer carrier layer.

14. The implement of claim 13, wherein the at least one nanosized or microsized material comprises a nano-sized hydroxyapatite particles.

15. The implement of claim 13, wherein at least one of the bioresorbable polymer carriers layer further comprises nano-sized or microsized metal particles.

16. The implement of claim 13, wherein at least one of the bioresorbable polymer carrier layers further comprises nano-sized or microsized metal oxide particles.

17. The implement of claim 13, wherein at least one of the bioresorbable polymer carrier layer further comprises nano-sized or microsized carbon particles.

18. The implement of claim 1, wherein at least one of the bioresorbable polymer carrier layers further comprises at least one bioactive material within the at least one bioresorbable polymer carrier layer.

19. The implement of claim 18, wherein the at least one bioactive material comprises a material selected from the group consisting of proteins, enzymes, growth factors, amino acids, bone morphogenic proteins, and platelet derived growth factors.

20. The implement of claim 18, wherein the bioresorbable polymer carrier layer further comprises vascular endothelial growth factors.

21. The implement of claim 1, wherein the bone or tissue forming material comprises at least one bioactive material.

22. The implement of claim 21, wherein the at least one bioactive material comprises a material selected from the group consisting of proteins, enzymes, growth factors, bone morphogenic proteins, platelet derived growth factors, extracellular matrix proteins, and fibronectin.

23. The implement of claim 1, wherein the bone or tissue forming material further comprises cells.

24. The implement of claim 23, wherein the cells comprise cells selected from the group consisting of stem cells, mesenchymal cells, osteoblasts, fibroblasts, endothelial cells, epithelial cells, nerve cells, glial cells, astrocytes, mammary cells, hepatocytes, muscle cells, islet cells, and chondrocytes.

25. The implement of claim 1, wherein the bone or tissue forming material comprises a growth factor.

26. The implement of claim 1, wherein at least one of the polymer carrier layers comprises a growth factor.

27. The implement of claim 1, wherein the bone or tissue forming material comprises a bone morphogenic protein.

28. The implement of claim 1, wherein at least one of the polymer carrier layers comprises a bone morphogenic protein.

* * * * *